United States Patent
Aluigi et al.

(10) Patent No.: US 11,344,499 B2
(45) Date of Patent: May 31, 2022

(54) NANOPARTICLES AS DELIVERY VEHICLES OF ACTIVE INGREDIENTS AND METHODS FOR THE PRODUCTION THEREOF

(71) Applicant: CONSIGLIO NAZIONALE DELLE RICERCHE, Rome (IT)

(72) Inventors: Annalisa Aluigi, Bologna (IT); Greta Varchi, Zola Predosa (IT); Giovanna Sotgiu, Ozzano dell'Emilia (IT); Andrea Guerrini, Forli (IT); Marco Ballestri, Bologna (IT)

(73) Assignee: CONSIGLIO NAZIONALE DELLE RICERCHE, Rome (IT)

(*) Notice: Subject to any disclaimer, the term of this patent is extended or adjusted under 35 U.S.C. 154(b) by 0 days.

(21) Appl. No.: 16/622,402

(22) PCT Filed: Jun. 13, 2018

(86) PCT No.: PCT/EP2018/065590
§ 371 (c)(1),
(2) Date: Dec. 13, 2019

(87) PCT Pub. No.: WO2018/229093
PCT Pub. Date: Dec. 20, 2018

(65) Prior Publication Data
US 2020/0206138 A1 Jul. 2, 2020

(30) Foreign Application Priority Data
Jun. 16, 2017 (IT) .................. 102017000067430

(51) Int. Cl.
*A61K 9/16* (2006.01)
*A61P 35/00* (2006.01)
(Continued)

(52) U.S. Cl.
CPC .............. *A61K 9/1658* (2013.01); *A61K 8/65* (2013.01); *A61K 9/0014* (2013.01); *A61K 31/20* (2013.01);
(Continued)

(58) Field of Classification Search
None
See application file for complete search history.

(56) References Cited

U.S. PATENT DOCUMENTS

| 5,736,371 A | 4/1998 | Samain et al. |
| 2003/0166507 A1* | 9/2003 | Li .................... A61K 47/59 |
| | | 514/449 |

(Continued)

FOREIGN PATENT DOCUMENTS

CN   105343870 A   *   2/2016

OTHER PUBLICATIONS

Helan Xu, Zhen Shi, Narendra Reddy, and Yiqi Yang. "Intrinsically Water-Stable Keratin Nanoparticles and Their in Vivo Biodistribution for Targeted Delivery." Journal of Agricultural and Food Chemistry, vol. 62, 2014, pp. 9145-9150. (Year: 2014).*

(Continued)

*Primary Examiner* — Isaac Shomer
(74) *Attorney, Agent, or Firm* — Lucas & Mercanti, LLP

(57) ABSTRACT

A nanoparticle comprising a keratin polypeptide and at least one lipophilic active ingredient, wherein the at least one lipophilic active ingredient is non-covalently bound to the keratin polypeptide and can be e.g. a therapeutic or diagnostic agent, a nutraceutical, a cosmetic ingredients, a dye or a cosmeceutical, the keratin polypeptide being water-soluble; optionally, the nanoparticle further comprises at least one hydrophilic active ingredient non-covalently bound to the keratin polypeptide, which can be e.g. a (Continued)

therapeutic or diagnostic agent, a nutraceutical, a cosmetic ingredients, a dye or a cosmeceutical.

20 Claims, 5 Drawing Sheets

(51) Int. Cl.
    *A61K 8/65*     (2006.01)
    *A61K 9/00*     (2006.01)
    *A61K 31/20*     (2006.01)
    *A61K 31/337*     (2006.01)
    *A61K 31/704*     (2006.01)

(52) U.S. Cl.
    CPC .......... *A61K 31/337* (2013.01); *A61K 31/704* (2013.01); *A61P 35/00* (2018.01)

(56) References Cited

U.S. PATENT DOCUMENTS

| | | | | |
|---|---|---|---|---|
| 2010/0196302 A1* | 8/2010 | Vermelho | ................ | C12P 21/06 514/1.1 |
| 2015/0274693 A1* | 10/2015 | Baibas | ................ | C07D 235/02 514/278 |
| 2017/0051027 A1* | 2/2017 | Van Dyke | ................ | A61L 15/32 |
| 2017/0183320 A1* | 6/2017 | Frangioni | ............ | C07D 279/20 |

OTHER PUBLICATIONS

Yanmei Li, Xuelian Zhi, Jiantao Lin, Xin You, Jiang Yuan. "Preparation and characterization of DOX loaded keratin nanoparticles for pH/GSH dual responsive release." Materials Science and Engineering C 73 (2017) pp. 189-197, available online Dec. 15, 2016. (Year: 2016).*

Manuela Curcio, Barbara Blanco-Fernandez, Luis Diaz-Gomez, Angel Concheiro, and Carmen Alvarez-Lorenzo. "Hydrophobically Modified Keratin Vesicles for GSH-Responsive Intracellular Drug Release." Bioconjugate Chemistry, vol. 26, 2015, pp. 1900-1907. (Year: 2015).*

A. Aluigi, G. Sotgiu, C. Ferroni, S. Duchi, E. Lucarelli, C. Martini, T. Posati, A. Guerrini, M. Ballestri, F. Corticelli and G. Varchi. "Chlorin e6 keratin nanoparticles for photodynamic anticancer therapy." RSC Advances, vol. 6, 2016, pp. 33910-33918. (Year: 2016).*

English Translation of CN 105343870 A. Obtained by examiner on Apr. 21, 2021. Originally published in Chinese on Feb. 24, 2016, 7 pages. (Year: 2016).*

Qinmei Li et al. "Biological stimuli responsive drug carriers based on keratin for triggerable drug delivery." Journal of Materials Chemistry, vol. 22, 2012, pp. 19964-19973. (Year: 2012).*

Yanmei Li, et al., "Preparation and Characterization of Dox Loaded Keratin . . . ", Materials Science and Engineering C, vol. 73, pp. 189-197, 2017.

Qinmei Li, et al., "Biological Stimuli Responsive Drug Carriers Based on Keratin . . . ", Journal of Materials Chemistry Royal Society of Chemistry UK, vol. 22, No. 37, pp. 19964-19973, 2012.

Manuela Curcio, et al., "Hydrophobically Modified Keratin Vesicles . . . ", Bioconjugate Chemistry, vol. 26, No. 9, pp. 1900-1907, 2015.

Ju Wang, et al., "Development of Feather Keratin Nanoparticles and Investigatigation . . . ", Materials Science and Engineering C, vol. 68, pp. 768-773, 2016.

Farzaneh Ebrahimgol, et al., "Electrosprayed Recoved Wool Keratin Nanoparticles", vol. 25, No. 9, pp. 1001-1007, 2014.

International Search Report and Written Opinion for International Application No. PCT/EP2018/065590 (11 Pages) (dated Sep. 27, 2018).

* cited by examiner

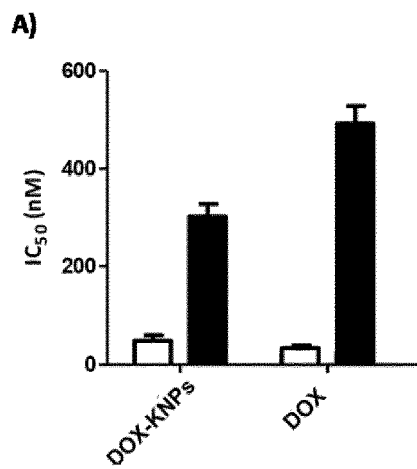
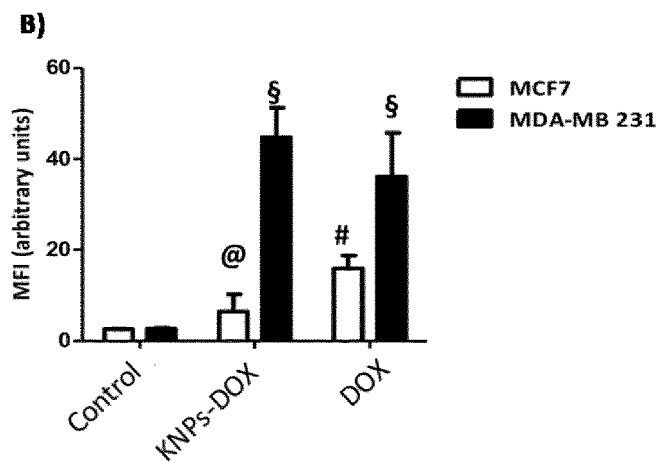
FIGURE 7A
FIGURE 7B
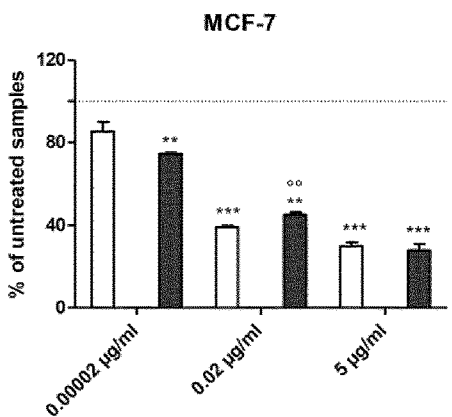
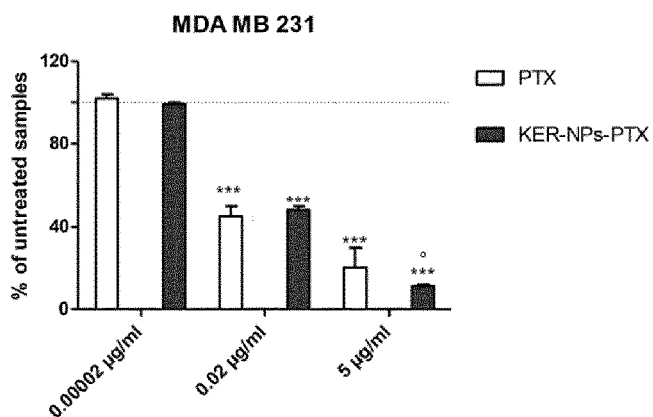
FIGURE 8A
FIGURE 8B
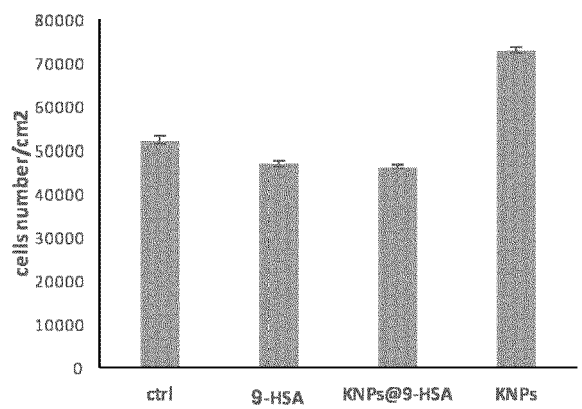
FIGURE 9

NANOPARTICLES AS DELIVERY VEHICLES OF ACTIVE INGREDIENTS AND METHODS FOR THE PRODUCTION THEREOF

CROSS-REFERENCE TO RELATED APPLICATIONS

This application is a 371 of PCT/EP2018/065590, filed Jun. 13, 2018, which claims the benefit of Italian Patent Application No. 102017000067430, filed Jun. 16, 2017.

FIELD OF THE INVENTION

The present invention relates to the field of the pharmaceutical, healthcare and cosmetic industry.

In particular, the invention concerns delivering/formulating active ingredients, such as drugs, prodrugs, nutraceuticals, diagnostic agents, therapeutics, cosmetics, cosmeceuticals, dyes, organic and inorganic compounds with a polypeptides molecule. Specifically, the invention concerns the use of hydrosoluble keratin and chemically modified hydrosoluble keratin for the production of keratin and keratin-modified nanoparticles incorporating active ingredients, to be either delivered to cells and tissues, or to be included into composites, formulations and advanced functional materials in order to improve materials features, such as antibacterial, antioxidant and antiaging properties; etc.

Methods for nanoparticles preparation, compositions and formulations that involve the keratin nanoparticles of the present invention are also described.

Background of the Invention

The development of nanoparticles as delivery/formulation systems for the release of molecules and ingredients has shown great potential in recent years.[1], [2]

Numerous documents deal with the incorporation of molecules, such as drugs, nutraceuticals, cosmetics and a broad spectrum of active ingredients with low water solubility or high metabolic degradation rate, into micelles, liposome, nano-capsules or nanoparticles. Several methods are available for the preparation of nanoparticles.[3], [4] In comparison to microsphere vehicles, nanoparticles possess advantages of having smaller diameters, larger surface area, better capability to penetrate into cells and tissues, and for being dispersed into composite materials with advanced functions. [5]

Natural biopolymers have attracted increasing attention especially as nanoparticulate drug delivery vehicles, because of their biocompatibility and large availability. [6]

Among natural polymers, proteins could be preferred in active ingredients loading because of their structural characteristics.[7], [8] Proteins can carry positive or negative charges at pH values below or above their isoelectric points, respectively, and, thus, could facilitate loading of molecules with different charges. Moreover, proteins have hydrophobic domains in their molecular structures and, hence, could attract hydrophobic molecules as well, such as water-insoluble compounds.

Among the natural proteins that are being studied for nanoparticles development, keratin could be highly preferred due to its cysteine-rich structure formed in the epithelial cells of higher vertebrates. After collagen, it is the most important biopolymer found in animals and possesses excellent biological compatibility and low immunogenicity and toxicity to cells.[9] Keratin is a chief component found in hair, skin, fur, wool, horn, nails and feathers. It has a high content of cysteine, glutamic acid, glycine and serine, and a large number of hydroxyl amino acids.

Keratin-based materials have emerged as potential candidates for many biomedical, biotechnological and advanced material-based applications due to their intrinsic biocompatibility, biodegradability, mechanical durability, and natural abundance. [10].

Li et al [2] describe the chemical functionalization of keratin (14-15 kDa) with polyethylene glycol and its use for the formation of nanoparticles incorporating the water-soluble drug doxorubicin. The keratin described in this document cannot be sufficiently dissolved in mild aqueous media, so the authors need to graft poly(ethylene glycol) onto the keratin backbone, affording keratin-PEG copolymers, which have an amphiphilic degree suitable for forming nanoparticles. The highest doxorubicin content in the keratin-g-PEG nanoparticles reached as high as 18.1% (w/w).

Curcio et al., [5] describe a hydrophobically modified keratin. In particular, polyethylene glycol-40 stearate was chosen as hydrophobic block to be coupled to keratin via radical grafting in order to confer the right amphiphilic degree to the protein. The PEG-stearate-modified keratin was then used to produce polymerasomes, which were obtained by employing a water-addition/solvent-evaporation method and loaded with both hydrophilic methotrexate and hydrophobic curcumin. In particular, curcumin could be entrapped into the nanoparticles thanks to the presence of the lipophilic copolymer covalently bounded to keratin.

S. Kunjiappan et al., [6] describe the use of keratin for the co-delivery of flavonoids rutin and quercetin complexes. In particular, it is disclosed the extraction of keratin form human hair which results in a protein with low water solubility: 1 mg of keratin in 50 mL of water plus the addition of 5 mg surfactant, chosen among SDS or sodium lauryl sulphate or Tween-20 SDS.

J. Yuan et al., [11] describe the use of keratin for the delivery of doxorubicin. The authors synthetize the particles by desolvation method starting from a keratin solution in water and by adding ethanol and glutaraldehyde for stabilize the nanoparticles, which then needed diverse steps of purification to get rid of reactants excess, e.g. ethanol and glutaraldehyde. The drug was loaded on the nanoparticles by electrostatic interaction. After loading, at least three cycles of purification were required in order to remove the excess of drug.

However, the keratin so far studied for the nanoparticles production provides particles with poor or no stability under aqueous environments.

As a matter of fact, according to the above prior art documents, chemical modification of keratin, e.g. through PEGylation, or addition of cross linkers and/or surfactants are the only available ways to obtain water stable keratin nanoparticles either nude or loaded with an active ingredient.

However, the chemical modification of the protein, such as for protein PEGylation, is an additional chemical process, which in turn requires a fine tuning of the process, additional purification/characterization steps and constitute a potential problem from the chemical regulation standpoint; in addition, the cross-linking of the protein could be easily disturbed by ions and pH in aqueous environment, when physically performed, or may have the issues of toxicity of remaining cross-linkers or low cross-linking efficiency of nontoxic cross-linkers.

Alternatively, prior art documents foresee the use of a very large amount of surfactants and/or emulsifiers in order to guarantee a satisfactory stability of the nanoparticles in an aqueous medium. However, large amount of surfactants is incompatible with many formulations in pharmaceutical and cosmetic industry.

Moreover, in all reported procedures several purification steps, such as dialysis, centrifugation, ultra-filtration, etc., are required to obtain pure keratin nanoparticles loaded with active ingredients, thus entailing loss of nanoparticles formation yield and drug loading efficiency.

Thus, the objective technical problem on which the present invention is based is that of providing keratin nanoparticles which are hydrosoluble without the mandatory presence of any emulsifier and/or surfactant, are able to load a high amount of at least one lipophilic active ingredient and are obtained according to a method which does not result in cross-linking of the nanoparticles, thus avoiding the above-mentioned instability and toxicity of the nanoparticles due to the presence of cross-linkers, and the compulsory need of nanoparticles purification.

SUMMARY OF THE INVENTION

Such problem was solved, according to the invention, by a nanoparticle comprising a keratin polypeptide and at least one lipophilic active ingredient, wherein said at least one lipophilic active ingredient is non-covalently bound to said keratin polypeptide and said keratin polypeptide is water-soluble.

Preferably, the at least one lipophilic active ingredient is selected from the group consisting of therapeutic agents, diagnostic agents, nutraceuticals, cosmetic ingredients, dyes and cosmeceuticals.

Preferably, said nanoparticle further comprises at least one hydrophilic active ingredient non-covalently bound to said keratin polypeptide.

Preferably, the at least one hydrophilic active ingredient is selected from the group consisting of therapeutic agents, diagnostic agents, nutraceuticals, cosmetic ingredients, dyes and cosmeceuticals.

Preferably, the at least one lipophilic active ingredient is a therapeutic agent selected from the group consisting of anticancer drugs, anti-inflammatory agents, antimicrobial agents, analgesics, hormones, anaesthetic agents, antianginals; anti-arrhythmic drugs; antibacterial and antiprotozoal agents; anti-coagulants; antidepressants; anti-diabetic drugs; anti-epileptic drugs; antifungal agents; antihistamines; anti-hypertensive drugs; anti-muscarinic agents; antineoplastic agents; anti-migraine drugs; anti-parasitic agents; anti-Parkinsonian drugs; antipsychotic, hypnotic and sedating agents; anti-stroke agents; anti-thrombotic agents; antitussives; antivirals; beta-adrenoceptor blocking agents; calcium channel blockers; cardiac inotropic agents; contraceptive agents; corticosteroids; dermatological agents; diuretics; gastro-intestinal agents; haemostatics; local anaesthetics; opioid analgesics; parasympathomimetics; peptides; steroids; stimulating agents; vasodilators, preferably anticancer drugs.

Preferably, the therapeutic agent is an anticancer drug, preferably selected from the group consisting of methotrexate, cisplatin; 5-fluorouracil, thiotopotecan, thiocamptothecin, camptothecin, paclitaxel, docetaxel, doxorubicin, bicalutamide, MDV3100, 9-hydroxyl stearic acid, 5-fluorouracil, curcumin, topotecan, irinotecan hydrochloride, vinblastine, histone methyltransferases inhibitors, carboplatin, methylene blue, AzureA, porphyrins and chlorins.

Preferably, the at least one hydrophilic active ingredient is a therapeutic agent selected from the group consisting of anticancer drugs, anti-inflammatory agents, antimicrobial agents, analgesics, hormones, anaesthetic agents, antianginals; anti-arrhythmic drugs; antibacterial and antiprotozoal agents; anti-coagulants; antidepressants; anti-diabetic drugs; anti-epileptic drugs; antifungal agents; antihistamines; anti-hypertensive drugs; anti-muscarinic agents; antineoplastic agents; anti-migraine drugs; anti-parasitic agents; anti-Parkinsonian drugs; antipsychotic, hypnotic and sedating agents; anti-stroke agents; anti-thrombotic agents; antitussives; antivirals; beta-adrenoceptor blocking agents; calcium channel blockers; cardiac inotropic agents; contraceptive agents; corticosteroids; dermatological agents; diuretics; gastro-intestinal agents; haemostatics; local anaesthetics; opioid analgesics; parasympathomimetics; peptides; steroids; stimulating agents; vasodilators, preferably anticancer drugs.

In an aspect of the invention, the keratin polypeptide is a wild-type keratin polypeptide.

In another aspect of the invention, the keratin polypeptide is a chemically modified keratin polypeptide.

In a further aspect of the invention, the keratin polypeptide is a mixture of a wild-type keratin polypeptide and a chemically modified keratin polypeptide.

Preferably, the nanoparticle contains an amount of said at least one lipophilic active ingredient ranging from 5% to about 45% by weight of the weight of said nanoparticle.

Preferably, the nanoparticle has a diameter between 1 nm to 400 nm, preferably between 100-200 nm.

In an aspect of the invention, the nanoparticle is for use in the treatment of neoplastic disease in a patient in need thereof, wherein the neoplastic diseases are selected from the group consisting of breast cancer, ovarian cancer, prostate cancer, lung cancer, colon cancer, colorectal cancer, pancreatic cancer, gastrointestinal stromal tumor, adrenal cancer, skin melanoma, non-skin melanoma, mouth cancer, eye tumor, nasal cavity and paranasal sinus cancer, penile cancer, bronchial carcinoma, heart cancer, uterine body cancer, cervical cancer, esophageal cancer, liver cancer, metastatic pancreatic cancer, lymphomas (Hodgkin, non-Hodgkin, cutaneous lymphoma, pediatric lymphomas), laryngeal cancer, pharyngeal cancer, malignant mesothelioma, leukemias (hairy cell leukaemia, chronic lymphocytic leukaemia, Acute lymphoblastic leukaemia, acute myeloid leukaemia, chronic myeloid leukaemia, pediatric leukemia), multiple myeloma, sarcomas, gliomas, renal cancer, testicular cancer, thyroid cancer, soft tissue sarcoma, bone sarcoma, Ewing sarcoma, Kaposi sarcoma, extraskeletal Ewing sarcoma, chondrosarcoma, osteosarcoma, metastatic bone cancer, choriocarcinoma, pineal gland cancer, salivary gland tumors, hypophysis cancer, primitive neuroectodermal tumour, multiple endocrine neoplasia type 1 (MEN1), Multiple Endocrine Neoplasia Type 2 (MEN2), bladder cancer, tumors of the pelvic organs, ureteral cancer, oral cavity cancer, anal cancer, vulvar cancer, vaginal cancer, spleen cancer, brain tumors, embryonal tumors, gall-bladder cancer, bile duct cancer, cancer cachexia, neuroblastoma cancer, pediatric neuroblastoma cancer, neuroendocrine cancer, pediatric tumors and Myeloproliferative neoplasms.

In another aspect, the present invention relates to the above-described nanoparticle for use in the treatment of dermatological diseases by topical application.

In an aspect thereof, the present invention discloses a method for producing the above-mentioned nanoparticle, comprising the steps of:

a) dissolving the keratin polypeptide in water or in a buffered aqueous solution at concentrations ranging from 1 to 5 mg/mL at room temperature, obtaining a solution;

b) filtering said solution;

c) adding said at least one lipophilic active ingredient previously dissolved in a proper solvent to said solution obtained in step b) under stirring.

In an aspect thereof, the present invention also discloses a pharmaceutical composition comprising the above-mentioned nanoparticles and a pharmaceutically acceptable carrier.

Preferably, the pharmaceutical formulation is for parenteral or oral administration.

Preferably, the pharmaceutical formulation is for use in the treatment of neoplastic diseases.

In an aspect the invention, the pharmaceutical formulation is for topical application, for use in the treatment of dermatological diseases.

In another aspect thereof, the present invention discloses a cosmetic formulation for topical application, comprising the above-mentioned nanoparticles and a cosmetically acceptable vehicle.

In a further aspect thereof, the present invention discloses a functional food comprising the above-mentioned nanoparticles, which is preferably selected from the group comprising cereal bars, yogurt and the like dairy products, bakery products, fruit juices and drinks in general.

The present invention is based on the finding that incorporation of one or more active ingredients (up to four ingredients), such as a drug, a nutraceutical, a cosmetic, an imaging agent, an antibacterial compound, a food supplement, a dye, an organic or inorganic compound into a nanoparticle that includes hydrosoluble keratin, provides an enhancement of the active ingredient properties.

Advantageously, the hydrosoluble keratin nanoparticles according to the present invention improve the water solubility (when lipophilic), bioavailability and efficacy of the loaded active ingredients, while reducing their tissue toxicity. Moreover, the loading of a cosmetic ingredient into said hydrosoluble keratin nanoparticles may promote tissues penetrability, while fostering tissue regeneration due to the intrinsic properties of keratin.

Another advantage of the keratin nanoparticles according to the present invention lies in the absence of any kind of covalent binding between the active ingredient and keratin. The active ingredient is loaded into the keratin nanoparticles by means of aggregation, lipophilic interaction or ionic gelation methods, which do not lead to the formation of any covalent binding but still ensure the stability of the nanoparticles in aqueous physiological media, with no need of any cross-linkers and surfactants.

In fact, the Applicants have surprisingly found that the nanoparticles according to the present invention are able to load a very high amount of an active ingredient (or of more active ingredients), namely up to 75% by weight of the keratin weigh, without the need to covalently bind the active ingredient(s) to the keratin, and this loading results to be very stable.

Moreover, according to the present invention, the keratin nanoparticles can also comprise two or more active ingredients with different water solubility degrees, namely at least one hydrophilic ingredient and at least one hydrophobic ingredient, at the same time.

This possibility of loading such different active ingredients allows the freedom to choose the most suitable active ingredients for a specific disease irrespective of their water solubility, which is a crucial parameter to guarantee the correct delivery of the active ingredients to the targeted organ or tissue.

Another advantage of the keratin nanoparticles of the present invention is that the water soluble keratin allows the stable incorporation of lipophilic active ingredients in quantitative yield and with no need of purification steps and avoiding the use of additives such as emulsifiers and surfactants to guarantee the stability of the nanoparticles in aqueous media.

The absence of such additives results in nanoparticles that are more suitable for all the applications (including therapeutic applications) in which it is required the stability of the nanoparticles in physiological media.

Another advantage of the keratin nanoparticles of the present invention is that they are formed with no need of chemical modification of the keratin polypeptide, such as trough the covalent bonding with polyethylene glycol, as reported for known keratin nanoparticles.

Another advantage of the keratin nanoparticles of the present invention is that the yield of active ingredient loading is quantitative.

Another advantage of the keratin nanoparticles of the present invention is that they do not need any purification step, which is very convenient from an industrial point of view.

According to another aspect of the invention, the hydrosoluble keratin can be suitably modified in order to improve its selectivity for specific cells and tissues, or to improve its physico-chemical properties, while maintaining water solubility. As an instance, keratin polypeptides can be chemically modified with dextran or polyethylene glycol chains [12] in order to avoid fast clearance from the body after administration. Dyes can be covalently linked to the protein in order to track the nanoparticles pathway within cells and/or tissues.

Furthermore, the nanoparticles of the present invention allow to dissolve in water highly lipophilic active ingredients through a straightforward, high-yielding and simple method. In turn, these formulations greatly expand the possible applications and efficacy of said active ingredients avoiding the use of toxic solvents.

A "polypeptide" as used herein refers to a consecutive series of 2 or more amino acids and as used herein, a "polypeptide" comprises the term "protein". Therefore, in some embodiments, the polypeptide comprises a consecutive series of at least 10 to 800 amino acids.

The expression "modified keratin" as used herein refers to a keratin polypeptide including one or more additional amino acid residues at the C-terminus or N-terminus of the consecutive sequence of amino acids of the keratin polypeptide.

In particular, the modified keratin polypeptide has at least 50% to 99% sequence homology to a known wild type keratin protein; the keratin polypeptide may include a chemical functionalization with organic compounds at the N-terminus or hydroxyl, amino and thiol groups of amino acid side chains.

The expressions "water-soluble keratin" and "hydrosoluble keratin" are used herein as synonyms and are meant to indicate a keratin having a solubility in water or in a buffered isotonic solution of at least 150 mg/mL at a temperature of 25° C.

The expression "non-covalently bound" referred to the binding of the at least one active ingredient to the hydrosoluble keratin, as used herein, means that the loading of said active ingredient is very stable without the need to covalently bind it to said keratin. In particular, the active ingredient is bound to the hydrosoluble keratin by ionic interaction, hydrophobic interaction and/or Van der Waals forces, or a combination of these.

A "drug" as used herein references to any therapeutic or diagnostic agent. Therapeutic agents include agents that are used in the treatment and prevention of different pathologies, such as but not limited to, cancer, infectious diseases and skin-related pathologies. The drug may be a small molecule, a peptide, a polypeptide, a protein, a carbohydrate, an antibody, an antibody fragment, a DNA a RNA or a combination thereof.

Non-limiting examples of therapeutic agents include an anticancer agent, an anti-inflammatory agent, an antimicrobial agent, a hormone, an agent for treating degenerative diseases, an anaesthetic agent.

An "anticancer agent" as used herein comprises methotrexate, cisplatin; topotecan; 5-fluorouracil, thiotopotecan, thiocamptothecin, camptothecin, paclitaxel, docetaxel, doxorubicin, bicalutamide, MDV3100, 9-hydroxyl stearic acid, curcumin, irinotecan hydrochloride, vinblastine, histone methyltransferases inhibitors, carboplatin, methylene blue, AzureA, porphyrins, chlorins, taxol, taxotere, artesumate, thioirinotecan, chelating agents, anti-metabolites, antitumor antibodies, topoisomerase inhibitors, mitotic inhibitors, corticosteroids (for example, nitrogen mustard, nitroureas, alkyl sulfonates, triaziane, ethylene imine, 6-mercaptopurine, pemetrexed, prednisone, metilprednisolone, dexamethasone, actinomycin, asparaginases, bleomycin, busulfan, capecitabine, cyclophosphamide, cytarabine, chlorambucil, dacarbazine, daunorubicin, doxorubicin hydrochloride, epirubicin hydrochloride, etoposide, fludarabine phosphate, fluorouracil, gemcitabine, idarubicin hydrochloride, hydroxyurea, ifosfamide, melphalan, mercaptopurine, mitomycin, mitoxantrone, oxaliplatin, procarbazine, raltitrexed, steroids, streptozotocin, tegafur-uracil, temozolomide, tioguanine, thiotepa, vincristine sulphate, vindesine, vinorelbine), target-therapy drugs such as tyrosine kinase inhibitors, tyrosine kinase receptor inhibitors, cyclin-dependent kinase inhibitors, proteasome inhibitors, immunoproteasome inhibitors, DNA methyltransferase inhibitors, aromatase inhibitors, demethylase inhibitors, deacetylase inhibitors, poly-ADP-ribose polymerase inhibitors, intracellular signaling pathways inhibitors, angiogenesis, apoptosis-inducing drugs, immunotherapy drugs and monoclonal antibodies, and retinoic acid.

As used herein "cancer" and "neoplastic disease" comprise the following diseases: breast cancer, ovarian cancer, prostate cancer, lung cancer, colon cancer, colorectal cancer, pancreatic cancer, gastrointestinal stromal tumor, adrenal cancer, skin melanoma, non-skin melanoma, mouth cancer, eye tumor, nasal cavity and paranasal sinus cancer, penile cancer, bronchial carcinoma, heart cancer, uterine body cancer, cervical cancer, esophageal cancer, liver cancer, metastatic pancreatic cancer, lymphomas (Hodgkin, non-Hodgkin, cutaneous lymphoma, pediatric lymphomas), laryngeal cancer, pharyngeal cancer, malignant mesothelioma, leukemias (hairy cell leukaemia, chronic lymphocytic leukaemia, Acute lymphoblastic leukaemia, acute myeloid leukaemia, chronic myeloid leukaemia, pediatric leukemia), multiple myeloma, sarcomas, gliomas, renal cancer, testicular cancer, thyroid cancer, soft tissue sarcoma, bone sarcoma, Ewing sarcoma, Kaposi sarcoma, extraskeletal Ewing sarcoma, chondrosarcoma, osteosarcoma, metastatic bone cancer, choriocarcinoma, pineal gland cancer, salivary gland tumors, hypophysis cancer, primitive neuroectodermal tumour, multiple endocrine neoplasia type 1 (MEN1), Multiple Endocrine Neoplasia Type 2 (MEN2), bladder cancer, tumors of the pelvic organs, ureteral cancer, oral cavity cancer, anal cancer, vulvar cancer, vaginal cancer, spleen cancer, brain tumors, embryonal tumors, gall-bladder cancer, bile duct cancer, cancer cachexia, neuroblastoma cancer, pediatric neuroblastoma cancer, neuroendocrine cancer, pediatric tumors and Myeloproliferative neoplasms.

A "prodrug" as used herein references to any medicament, which is inactive until properly activated/metabolized within the body. The activation process and the release of the drug might occur upon internal or external stimulus, such as, but not limited to, enzyme action, pH, temperature, light and ultrasound. Not-limiting examples of prodrugs are: irinotecan, bis-TES-paclitaxel, enalapril, levodopa, pivampicillin, oseltamivir, tenofovir disoproxil, ximelagatran, MGS0210, estramustine phosphate, fosfluconazole, propofol phosphate, valganciclovir, latanoprost, tazarotene.

A "cosmetic ingredient" as used herein references to any chemical compound used in cosmetic products.

A "nutraceutical ingredient" as used herein references to any nutrients, dietary supplements and herbal products to be include in specific diets or processed foods such as, for example, vegetable/animal oils, vitamins, cholesterol, creatine, amino acids, mineral salts, beta-carotene, flavonoids, vegetable or yeast extracts, hyaluronic acid, inositol, herbs, and all the other ingredients listed in the EU Regulation no. 432/2012 and encompassing the definition of the Dietary Supplement Health and Education Act of 1994.

A "cosmeceutical ingredient" as used herein references to any cosmetic products having drug-like benefits to the body such as, for example, vitamins, alfa- and beta-hydroxyl acids, lipoic acid, dimethyl amino ethanol, glycolic acid, salicylic acid, hyaluronic acid.

A "dye" as used herein references to any organic or inorganic compound natural or synthetic to be used for colouring textiles, foods, hair, polymers, cells, tissues, etc, such as, for example, porphyrins, phtalocyanines, hair color dyes, dyes for coloring fabrics, organic and inorganic pigments for fabrics and polymer fabrics.

The expression "a cosmetic formulation" as used herein relates to a product having hydrating and preservative properties and which is able to treat keratin substrates, signs of aging, skin damages due to exposition to environment agents, thus improving the appearance of the skin.

The expression "dermatological disease" as used herein refers to any skin disease which may have visible or not-visible consequences, including: cell differentiation and proliferation diseases, keratinisation disorders, inflammatory and allergic disorders, sebaceous disorders, dermis diseases, malignant or not malignant epidermal proliferations, skin diseases caused by UV radiation, disease associated with aging, skin cicatrization diseases, scleroderma, miastenia gravis, organ rejection, endotoxin shock, sepsis, psoriasis, eczema, atopic dermatitis, bullous dermatitis, Louis-Bar's syndrome, Cowden's syndrome, dyskeratosis congenital, Rubinstein-Taybi's syndrome, Werner syndrome, xeroderma pigmentosum, multiple sclerosis, autoimmune thyroiditis, uveitis, systemic lupus erythematosus, Addison's disease, autoimmune polyglandular syndrome and Graves' disease.

The expression "treating keratin substrates" as used herein refers to any treatment aimed at preserving or restoring the healthy functioning of the skin and/or hair and/or nails or any treatment that provides means to preserve or improve their appearance and/or structure. Examples of such treatments include: skin strengthening, wrinkle reduction, moisturizing, protection from any kind of aggression, in particular, protection from sun radiations and aging indicators.

The expression "signs of aging" as used herein includes all the changes regarding the appearance of the skin due to aging and photo-aging. Examples of these changes include wrinkles and thin lines, floss skin, thin skin, loss of skin elasticity and/or tone, opaque skin. It also includes internal skin modifications that do not directly affect external appearance changes. An example of these internal modifications is the degradation that occurs internally to the skin due to repeated exposure to UV radiation.

The expression "improvement of the appearance of the skin" as used herein includes all phenomena that may result in a visual improvement of the skin appearance.

Examples of these phenomena lead to a skin with the more beautiful, firm and smooth skin, thus diminishing or removing all the small imperfections, such as the attenuation of skin orange "peel effect".

The term "external aggression" or "environment aggression" as used herein refer to aggressions that can be of chemical, physical, biological, or thermal origin.

The present invention also provides pharmaceutical compositions containing said hydrosoluble keratin nanoparticles and conventional, pharmaceutically acceptable and non-toxic carriers, excipients, adjuvants, rheology modifiers, surfactants and vehicles.

An "excipient" as used herein references to any substance formulated alongside the active ingredient of a medication, included for the purpose of long-term stabilization, bulking up solid formulations that contain potent active ingredients, or to confer a therapeutic enhancement on the active ingredient in the final dosage form, such as facilitating drug absorption, reducing viscosity, or enhancing solubility. Excipients can also be useful in the manufacturing process, to aid in the handling of the active substance concerned such as by facilitating powder flowability or non-stick properties, in addition to aiding in vitro stability such as prevention of denaturation or aggregation over the expected shelf life.

A "rheology modifier" as used herein references to any substance used for modifying the viscosity of an emulsion. Non-exhaustive examples of rheology modifiers are thickeners for cosmetics, paints, medicated gels, creams, ect.

A "surfactant" as used herein references to any compound able to lower the between two liquids or between a liquid and a solid. Non-exhaustive examples of surfactants may include, wetting agents, emulsifiers, foaming agents, dispersants, etc.

Said pharmaceutical compositions can be administered with any available and efficient delivery system, comprising, but not limited to, oral, buccal, parenteral, inhalation routes, by injection, or rectal route (for ex. by means of suppositories).

The administration by parenteral route comprises subcutaneous, intravenous, intramuscular, intrasternal injection or infusion techniques.

The solid dosage forms for the administration by oral route comprise, for example, capsules, tablets, powders, granules and gels. These dosage forms normally also comprise additional substances different from the inert diluents, such as, for example, lubricating agents like magnesium stearate.

The injectable preparations, for example aqueous or oily sterile injectable solutions or suspensions, may be formulated according to the known technique and by optionally using appropriate dispersing, wetting and/or suspending agents.

The pharmaceutical preparations according to the present invention may be produced by using conventional pharmaceutical techniques, as described in the various pharmacopoeias or handbooks of the field such as, for example, "Remington's Pharmaceutical Sciences Handbook", Mack Publishing, New York, 18th Ed., 1990.

BRIEF DESCRIPTION OF THE FIGURES

The following figures form part of the present invention and are included to further demonstrate certain aspects of the invention. The invention may be better clarified if referring to one or more of these drawings in combination with the detailed description of the specific embodiments presented herein.

FIGS. 7A and 7B represent bar graphs showing the $IC_{50}$ values (A) and DOX accumulation levels (B) obtained on MCF7 and MDA-MB 231 cells following 72 h exposure to KNPs-DOX and DOX. (*$p<0.05$ vs MCF7 and DOX same cell line; *** $p<0.0001$ vs MCF7; ° $p<0.01$ vs DOX and KNPs-DOX same cell line, @ $p<0.05$ vs control; #$p<0.05$ vs all the others same cell line; § $p<0.001$ vs MCF7 and control.

FIGS. 8A and 8B represent bar graphs showing the effects of PTX and KER-NPs-PTX on MCF-7 (A) and MDA MB 231 (B) cell proliferation in 2D model. Cell proliferation, after exposure to increasing concentrations of PTX (0.00002, 0.02, 5 µg/ml), was evaluated at 72 h by APH assay. Statistical significance versus untreated cells (represented by a dotted line):  $p<0.01$, * $p<0.001$. The y axis reports the percent of cell growth with respect to untreated cells (control), obtained by WST-1 absorbance.

FIG. 9 shows a bar graph showing the number of alive HT29 cells after treatment with 9-HSA as free or loaded on keratin nanoparticles.

DESCRIPTION OF ILLUSTRATIVE EMBODIMENTS

Figure 1:
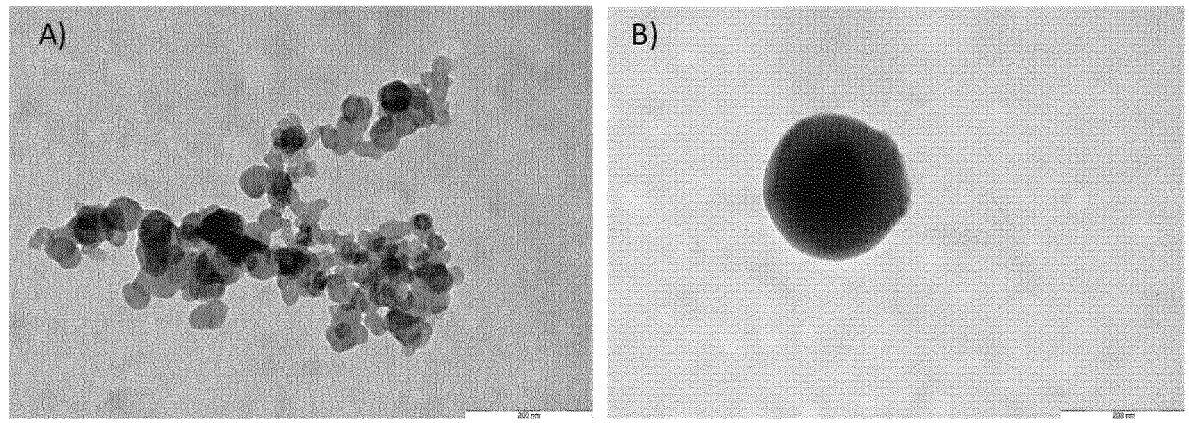
FIG. 1 shows the TEM images of taxol keratin nanoparticles at different magnifications. Images were recorded on a Gatan MSC794 Transmission Electron Microscope.

The present invention is based on the finding that keratin nanoparticles can be applied for the incorporation and delivery of at least one or more hydrophobic or of at least one or more hydrophobic and hydrophilic active ingredient. Moreover, keratin nanoparticles, as compared to other polypeptides and proteins, allow to stably incorporate high amount of the selected active ingredient, and to be easily re-suspended in green solvents such as water. As an example, taxol-keratin nanoparticles can efficiently cross tumour cells membrane and deliver the drug mainly at the target site. As a further example, vitamin A-keratin nanoparticles can be incorporated into cosmeceutical and nutraceuticals formulation in order to favour its uptake from cells and tissues.

A. Keratin and Modified Keratin

Keratin as used herein refers to a "polypeptide" comprising the term protein, which is constituted by a consecutive series of 2 or more amino acids and as used herein, and in some embodiments, the polypeptide comprises a consecutive series of at least 10 to 800 amino acids.

The polypeptide has at 50% to 99% sequence homology to a known wild type keratin protein.

The expression "modified keratin" as used herein refers to a keratin polypeptide including one or more additional amino acid residues at the C-terminus or N-terminus of the consecutive sequence of amino acids of the keratin polypeptide.

In particular, the modified keratin polypeptide has at least 50% to 99% sequence homology to a known wild type keratin protein; the keratin polypeptide may include a chemical functionalization with organic compounds at the N-terminus or hydroxyl, amino and thiol groups of amino-acid side chains.

B. Uses of Keratin and Keratin-Modified Nanoparticles

In general, the nanoparticles of the present invention include one or more hydrophobic active ingredient or at least one or more hydrophobic and hydrophilic active ingredient. An active ingredient may be a therapeutic agent, a diagnostic agent, a nutraceutical compound, a cosmeceutical compound, a cosmetic ingredient, a dye, an organic or inorganic compounds or a combination thereof to be either delivered to cells and tissues, or to be included into composites and advanced functional materials.

B.1. Hydrosoluble keratin and hydrosoluble modified-keratin nanoparticles for delivering lipophilic drugs and/or prodrugs (up to 4 different active ingredients): taxol, taxotere, doxorubicin, bicalutamide, 9-hydroxyl stearic acid, MDV3100, methotrexate, cisplatin; topotecan; 5-fluorouracil, thiotopotecan, thiocamptothecin, camptothecin, levodopa.

B.2. Hydrosoluble keratin and hydrosoluble keratin-modified for delivering (formulating) lipophilic cosmeceuticals and cosmetic ingredients (up to 4 different cosmetic ingredients): enalapril, levodopa, pivampicillin, oseltamivir, tenofovir disoproxil, ximelagatran, MGS0210, fosfluconazole, propofol phosphate, valganciclovir, latanoprost, tazarotene.

B.3. Hydrosoluble keratin and hydrosoluble keratin-modified for delivering (formulating) lipophilic nutraceuticals (up to 4 different nutraceuticals): vegetable/animal oils, vitamins, cholesterol, creatine, mineral salts, beta-carotene, flavonoids, vegetable or yeast extracts, hyaluronic acid, inositol, herbs.

B.5 Hydrosoluble keratin and hydrosoluble keratin-modified for delivering (formulating) lipophilic cosmeceuticals (up to 4 different cosmeceuticals): vitamin A, lipoic acid, dimethyl amino ethanol, glycolic acid, salicylic acid, hyaluronic acid.

B.4. Hydrosoluble keratin and hydrosoluble keratin-modified incorporating lipophilic dyes and active ingredients as additives for plastics and paints (up to 4 different dyes): porphyrins, phtalocyanines, fluorescent dyes, such as fluorescein, organic and inorganic pigments.

B.5 Hydrosoluble keratin and hydrosoluble keratin-modified for delivering a combination of hydrophilic, such as doxorubicin hydrochloride, methylene blue or AzureA and lipophilic drugs and prodrugs (point B.1) (up to 4 different compounds)

B.6 Hydrosoluble keratin and hydrosoluble keratin-modified for delivering a combination of products reported in B1 to B5.

C. Methods

The present patent application describes nanoparticles of hydrosoluble keratin or chemically modified hydrosoluble keratin for the incorporation of active ingredients through different techniques.

According to the present invention, the nanoparticles include:

i) a hydrosoluble keratin or a chemically modified hydrosoluble keratin polypeptide and ii) one or more lipophilic in combination or not with hydrophilic active ingredients, such as, but not limited to, a therapeutic compound, a prodrug, a nutraceutical, a cosmetic, an imaging agent, an antibacterial compound, a food supplement, a dye, an organic or inorganic compound, wherein the nanoparticles have a diameter of about 1 nm to about 500 nm, preferably between 100-200 nm.

Hydrosoluble keratin may be obtained from different sources, but in some particular embodiments hydrosoluble keratin is obtained from raw wool.

Figure 5:
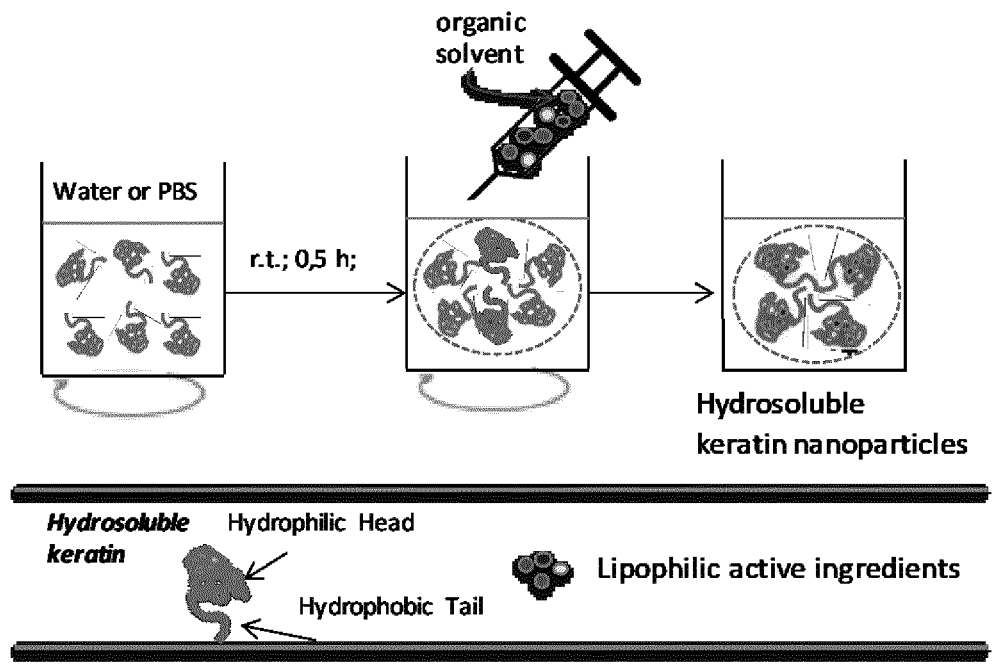
FIG. 5 shows a schematic representation of preparation of keratin nanoparticles loaded with lipophilic active ingredients through "aggregation induced by lipophilic compound".
Figure 6:
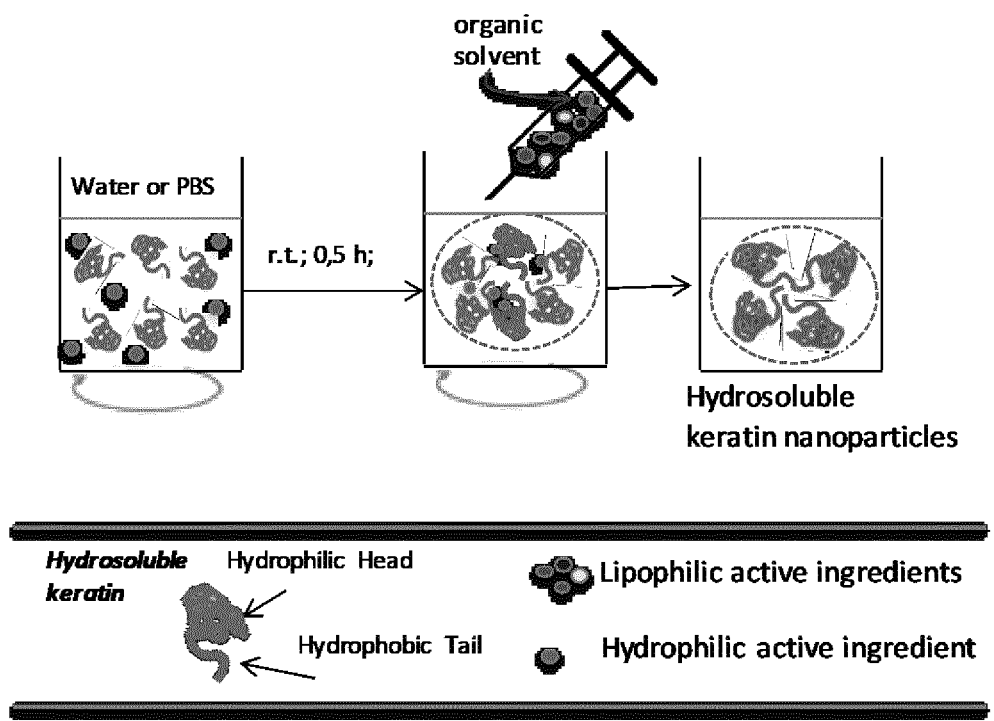
FIG. 6 shows a schematic representation of preparation of keratin nanoparticles loaded with lipophilic and hydrophilic active ingredients through "aggregation induced by lipophilic compound".

The method for incorporating the active ingredients into keratin nanoparticles may be selected among the following:

i) Aggregation method induced by a lipophilic active ingredient: one or more lipophilic active ingredients (1 to 4) are dissolved into the minimal amount of a properly selected organic solvent and added to a water solution of hydrosoluble keratin, as shown in FIG. 5;

ii) Aggregation method induced by a lipophilic active ingredient in presence hydrophilic active ingredients: one or more lipophilic active ingredients are dissolved into the minimal amount of a properly selected organic solvent and added to a water solution of hydrosoluble keratin possibly containing a hydrophilic active ingredient, as shown in FIG. 6;

iii) Ionic gelation/aggregation: the hydrophilic ingredient is dissolved in water at a proper concentration and added to keratin solution in order to induce nanoparticles formation by ionic gelation; after that the lipophilic drug dissolved in proper solvent is added to the gelated nanoparticles in order to complete the nanoparticle formation by aggregation In particular, for methods i) and ii), depending on the concentration of the active ingredients and of the keratin solution, the formation of the hydrosoluble keratin nanoparticles is induced by the lipophilic active ingredient, which acts as aggregating element.

All the described preparation methods allow to avoid dialysis, ultrafiltration and other possible purification procedures, while providing a maximum active ingredient loading efficiency.

EXAMPLES

Example 1

Materials and Methods. Raw wool was kindly donated from Cariaggi Fine Yarns, S.p.A. Keratin was extracted from raw wool by sulphitolysis reaction. Briefly, a fiber sample, withdrawn from a combed sliver and cleaned by Soxhlet extraction with petroleum ether, was washed with distilled water and dried at 21° C. and 60% relative humidity overnight. Afterward, cleaned fibers (5 g) were cut into snippets and dispersed in 100 mL of aqueous solution containing urea (8 M), sodium metabisulphite (0.5 M) and sodium dodecyl sulfate (SDS, 0.1 M), under mechanical shaking at 65° C. overnight. The mixture was filtered with a vacuum filter (10-16 μm cut-off), dialyzed against distilled water using a cellulose tube (molecular weight cut-off 12-14 kDa) for 3 days at room temperature, changing the distilled water four times a day. The resulting aqueous solution was freeze-dried in order to obtain pristine keratin powder.

General Method for the Preparation of Nanoparticles Through Aggregation Method.

The lipophilic compound was used as aggregating agent, able to induce the formation of hydrosoluble keratin nanoparticles. Keratin was extracted from raw wool according to a previously reported literature procedure [*Materials & Design* 2016, 110, 475-484].

In this method, keratin was dissolved in water (pH 6.5) or PBS (pH 5.5) or PBS (pH 7.4) or $NaHCO_3$ buffer (pH 9) at concentrations ranging from 1 to 10 mg/mL at room temperature for at least 1 h.

A desired amount of lipophilic compound dissolved in a proper solvent (compound concentration from 1 mg/mL to 10 mg/mL) was added to the keratin solution, under stirring at 750 rpm.

Specific, although non-comprehensive, examples of lipophilic compounds used for the preparation of hydrosoluble keratin nanoparticles (h-KNPs) through aggregation method are listed in Table 1 along with nanoparticles sizes and poly-dispersity index (PDI), as well as the maximum drug loading expressed as % in weight of drug with respect to nanoparticles.

TABLE 1

List of keratin nanoparticles obtained by aggregation and loaded with lipophilic active ingredients

| Entry | Starting solution | Lipophilic drug | Loading (% drug/keratin) | Particle size (nm)/PDI |
|---|---|---|---|---|
| 1 | Keratin solution 1 mg/mL; pH = 6.5 | β-Carotene in THF (1.5 mg/mL) | 5.66 | 180/0.15 |
| 2 | Keratin solution 1 mg/mL; pH = 6.5 | Vitamin E in EtOH (4.5 mg/mL) | 10 | 115/0.11 |
| 3 | Keratin solution 1 mg/mL; pH = 9 | 9-HSA in EtOH (10 mg/mL) | 6.7 | 245/0.03 |
| 4 | Keratin solution 1 mg/mL; pH = 6.5 or 7.4 | PTX in EtOH (10 mg/mL) | 28.6 | 150/0.15 |
| 5 | Keratin solution 1 mg/mL; pH = 6.5 or 7.4 | PTX in EtOH (10 mg/mL) | 43 | 165/0.15 |
| 6 | Keratin solution 1 mg/mL; pH = 6.5 or 7.4 | PTX-F35 in EtOH (6 mg/mL) | 16.6 | 210/0.25 |
| 7 | Keratin solution 2 mg/mL; pH = 9 | Doxorubicin in $H_2O$ (1 mg/mL) | 16.6 | 90/0.3 |
| 8 | Keratin functionalized with Ce6 (Ker-Ce6 20 μg/mg) | PTX in EtOH (10 mg/mL) | 16.6 | 155/0.15 |
| 9 | Keratin functionalized with Ce6 (Ker-Ce6 30 μg/mg) | PTX in EtOH (10 mg/mL) | 16.6 | 165/0.15 |
| 10 | Keratin functionalized with Ce6 (Ker-Ce6 20 μg/mg) | PTX-F35 in EtOH (10 mg/mL) | 8.8 | 260/0.22 |
| 11 | Keratin solution 1 mg/mL; pH = 6.5 or 7.4 | PTX in EtOH (10 mg/mL) Indocyanine green (ICG) | PTX: 16.6 ICG: 2.8 | 146/0.11 |
| 12 | Keratin solution 1 mg/mL; pH = 6.5 or 7.4 | Doxorubicin via gelation PTX in EtOH (10 mg/mL) | DOXO: 10 PTX: 10 or 20 | 170/0.25 |
| 13 | Keratin solution 1 mg/mL; pH = 6.5 or 7.4 | PTX in EtOH (10 mg/mL) IR780 | PTX: 9 IR780: 9 | 138/0.19 |
| 14 | Keratin-FITC 1 mg/mL; pH = 6.5 or 7.4 | 9-HSA in EtOH (10 mg/mL) | FITCH: 1 9-HSA: 6 | 180/0.2 |
| 15 | Keratin solution 1 mg/mL pH = 6.5 or 7.4 | Topotecan (1 mg/mL in H2O) PTX (10 mg/mL in EtOH) | TPC: 9 PTX: 16.6 | 158/0.25 |
| 16 | Keratin solution 1 mg/mL; pH = 6.5 or 7.4 | Azure A (10 mg/mL) PTX (10 mg/mL in EtOH) | AzA: 2.8 PTX: 13 | 160/0.22 |

Example 2—Preparation of Keratin Nanoparticles Loaded with Taxol Via Aggregation (KNPs-PTX)

Figure 2:
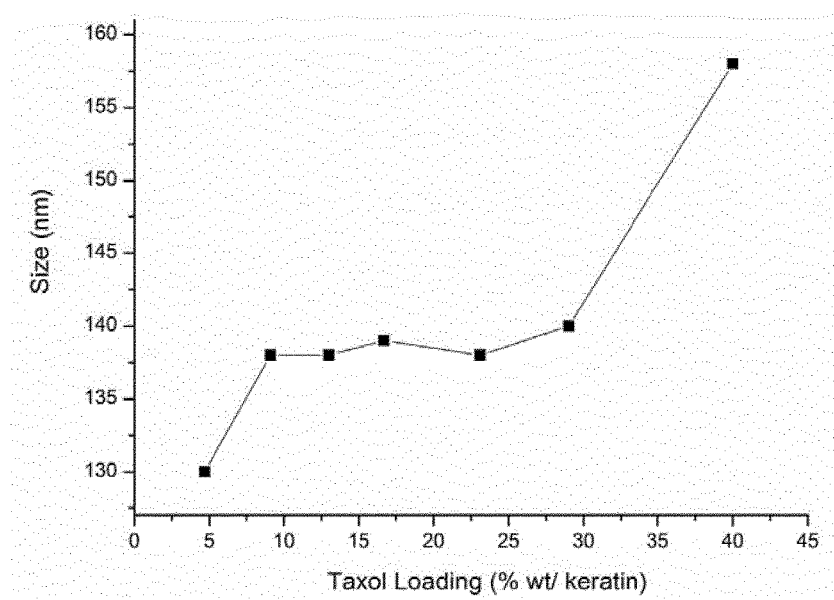
FIG. 2 shows a graph which represents the correlation between taxol loading (expressed in percentage weight ratio between taxol and keratin) and keratin nanoparticles dimensions (nm).
Figure 3:
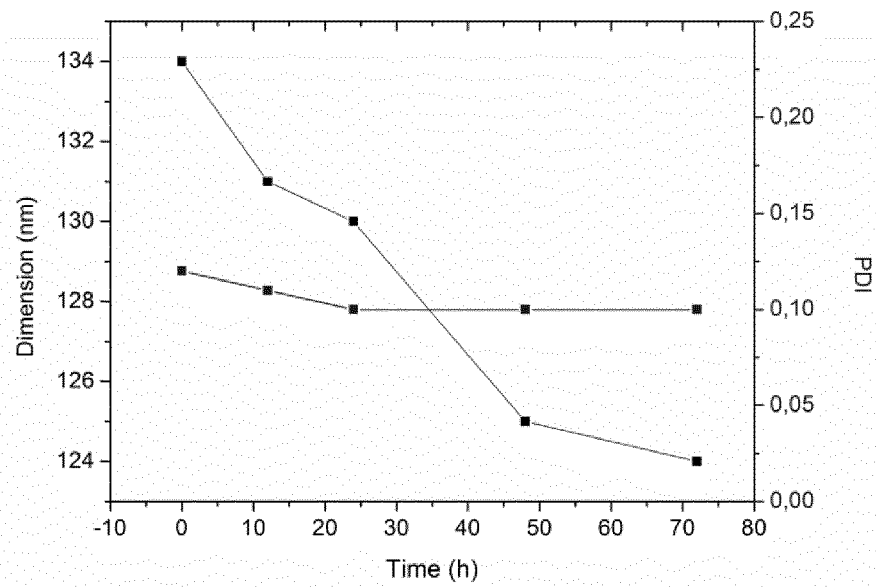
FIG. 3 represents a graph showing the stability of KNPs-PTX depending on the nanoparticles dimensions (nm), time (h) and polydispersity index (PDI), in physiological conditions.
Figure 11:
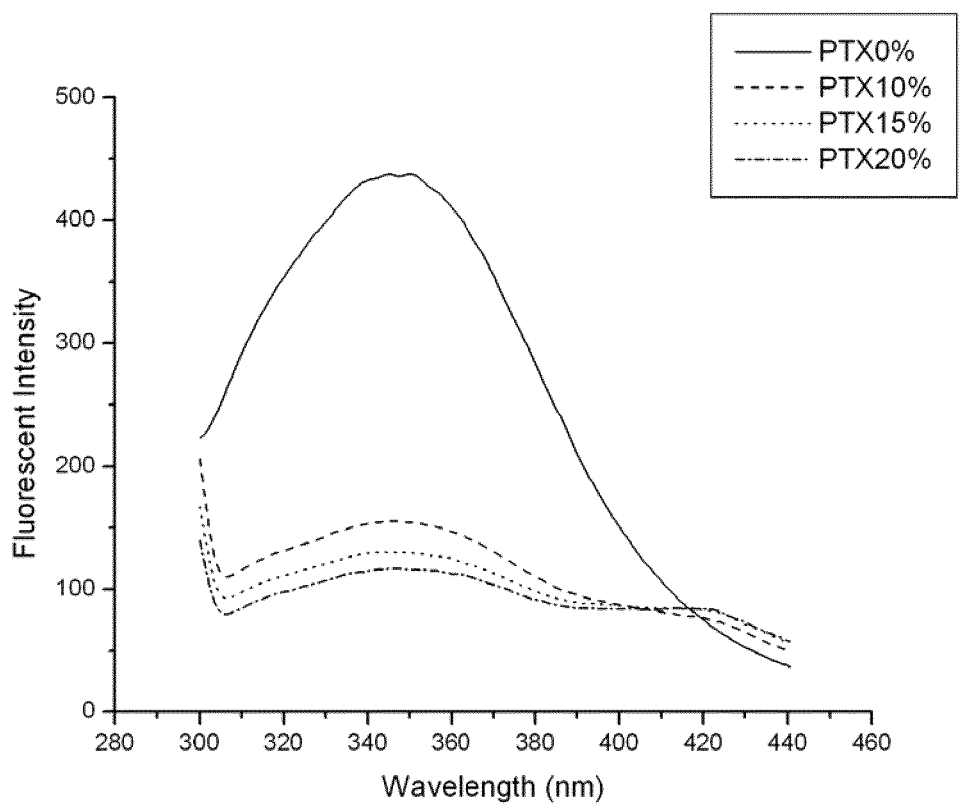
FIG. 11 shows a graph representing the interaction between PTX with keratin, that was determined by real-time fluorescence spectroscopy. The excitation wavelength was 277 nm. The fluorescence spectra show the reduction in the fluorescence intensity of keratin by subsequent addition of PTX.

This example describes the process by which keratin nanoparticles loaded with taxol can be obtained. Keratin, was dissolved in mQ water or PBS at a concentration of 1.5 mg/mL and filtered using a 450 nm filter cut-off. Different amounts of taxol dissolved in ethanol (10 mg/mL) were added to the keratin solution, under stirring at 730 rpm. Taxol induces the aggregation of keratin into nanoparticles (KNPs-PTX), whose dimensions and polydispersity index depend on taxol loading. In particular, it was found that low drug concentration (5% wt) yielded particles having a mean diameter of about 110 nm; while, with increasing the drug amount from 10 to 30% wt, the nanoparticles dimensions increase to 138 nm. By using a taxol amount of 40% wt nanoparticles having a mean diameter of 158 nm were obtained (FIG. 2). Real-time fluorescence spectroscopy was used to monitor the loading/interaction between PTX and keratin. Fluorescence spectra, obtained by exciting the samples at 277 nm (tryptophan absorbance peak) show the reduction in the fluorescence intensity induced on keratin by subsequent addition of PTX (FIG. 11).

Example 3—Preparation of Keratin Nanoparticles Loaded with Doxorubicin Via Aggregation (KNPs-Doxorubicin)

This example describes the process by which keratin nanoparticles loaded with doxorubicin can be obtained. Keratin is dissolved in carbonate buffer (pH 9) at a concentration of 4 mg/mL and filtered using a 450 nm filter cut-off.

Different amounts of doxorubicin dissolved in water (1 mg/mL) were added to the keratin solution, under stirring at 730 rpm. In particular, the amount of added doxorubicin, with respect to keratin was of 15% and 30% wt. In basic environment, the hydrophobic doxorubicin induces the keratin aggregation into nanoparticles, involving the hydrophobic part of the protein. The particles dimensions depend on the doxorubicin loading. It was found that nanoparticles of about 80 and 100 nm were obtained with a doxorubicin loading of 15 and 20% wt, respectively.

Example 4—Stability of KNPs-Taxol Nanoparticles

In order to evaluate the stability of KNPs-PTX in physiological conditions, 500 µg of keratin nanoparticles loaded with 16.6% wt of taxol, as obtained according to Example 2, were dissolved in 2 mL of PBS and maintained at 37° C. The nanoparticles dimension was controlled during time by dynamic light scattering measurements.

A slight decrease of nanoparticles diameter from 114 nm to 124 nm occurs within the first 72 h; while no significant changes can be observed for the polydispersity index. These data suggest a good stability on KNPs-PTX nanoparticles in physiological conditions.

Figure 4:
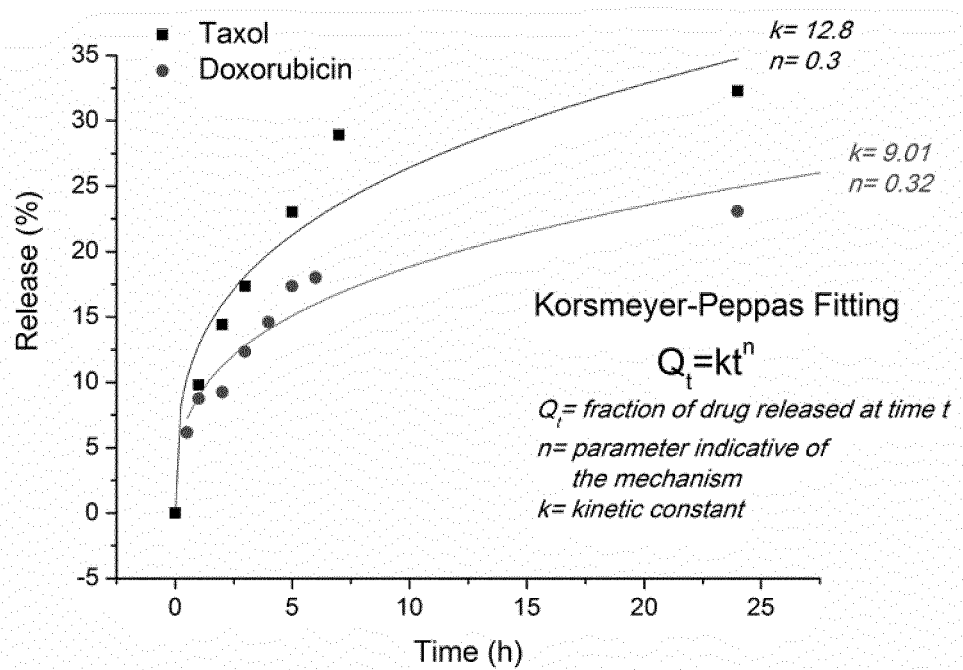
FIG. 4 represents a graph showing the percentage release of doxorubicin and taxol from keratin nanoparticles obtained by aggregation method.

Example 5—Drug Release Mechanism of Keratin Nanoparticles Prepared by Aggregation Induced from Lipophilic Drug In order to test the drug release mechanism of lipophilic drug from keratin nanoparticles, the KNPs-PTX and KNPs-DOXO prepared as previously described were placed into a dialysis bag (cut-off 12-14 kDa), subsequently immersed in PBS solution at pH 7.4 at 37° C., under shaking. A little amount of ethanol was used in the case of taxol release study. Periodically, 1 mL of the outer solution was withdrawn and 1 mL of fresh buffer was added to the system. The drug concentration in the outer buffer was determined by UV-Vis spectrophotometer. It was found that, at pH 7.4, which corresponds to the physiological conditions of the blood stream, only 32% of taxol and 23% of doxorubicin were released in the first 24 h. These data indicate that, under physiological conditions no burst release of the drug occur, which might be highly beneficial in case of drug delivery where you need and elevated control over drug position and concentration. Moreover, the release processes were described with the Korsmeyer-Peppas model. In this model, the "n" value characterizes the release mechanism of the drug. As shown in FIG. 4, the "n" values for both nanoparticles are lower than 0.45 (0.31 for taxol and 0.32 for doxorubicin), indicating a Fickian diffusion mechanism of drugs. The kinetic constant related to the KNPs-PTX (k=12) is higher than that related to KNPs-DOX (k=9) indicating a faster release of taxol compared to doxorubicin.

Example 6—Preparation of Chlorine e6 (Ce6) Conjugated Keratin Nanoparticles Via Aggregation Induced by Taxol This example describes the process by which keratin powder conjugated with different amount of chlorine e6 Ce6 is used to prepared nanoparticles loaded with taxol as described in Example 2. Keratin powders covalently functionalized with different amounts of Ce6, e.g. 20, 30, 50 µg/mg, were dissolved in PBS at a concentration of 1.5 mg/mL. The aggregation is induced by adding 20% of taxol dissolved in ethanol. Dimensions of keratin nanoparticles were 155 nm for Ker-Ce6 20 µg/mg and 165 nm for Ker-Ce6 30 µg/mg.

Example 7—Preparation of Keratin Nanoparticles Loaded with Doxorubicin and Taxol by Combining the Aggregation and Ionic Gelation Methods Both Induced by Drugs This example describes the process by which keratin nanoparticles loaded with a hydrophilic drug as doxorubicin in water and a lipophilic drug as taxol can be obtained.

Keratin was dissolved in mQ water at a concentration of 1 mg/mL and filtered using a 450 nm filter cut-off. Doxorubicin dissolved in water (1 mg/mL) was added to the keratin solution under stirring at 730 rpm as needed to obtain a final concentration of doxorubicin of 10% wt with respect to keratin. After stirring for 60 min, the solution was mildly centrifuged (400 g/5 min) in order to remove possible aggregates; afterwards, taxol dissolved in ethanol (10 mg/mL) was added to the keratin solution to obtain a final concentration of 20% wt with respect to keratin. The nanoparticles obtained by a combination of ionic gelation induced by doxorubicin and aggregation induced by taxol showed a final size of about 110 nm.

Example 8—In Vitro Internalization and Cytotoxicity Studies of KNPs Loaded with Doxorubicin The antiproliferative effect of the different DOX-loaded KNPs was assessed in human breast adenocarcinoma MCF7 and MDA-MB-231 cells by the MTT assay and compared to free DOX. Briefly, $3 \times 10^4$ cells/ml were seeded onto 96-well plates and allowed to grow for 24 h prior to treatment with different concentrations of DOX or DOX-loaded KNPs (the range of DOX concentrations used was 5-2000 nM). After 72 h, MTT (5 DM in PBS) was added to the cells for 3 h at 37° C. Formazan crystals, formed by mitochondrial reduction of MTT, were dissolved in DMSO and the absorbance was read at 570 nm using a Universal Microplate Reader EL800 (BioTek Instruments). $IC_{50}$ values were determined by using the median effect equation.

Generally, $IC_{50}$ is a pharmacokinetic measure of drug concentration at which 50% of the target is inhibited. Therefore, a drug with a lower $IC_{50}$ value allows to achieve the desired effect using less quantity than that to be used if a drug with a higher $IC_{50}$ value is provided.

FIG. 7A clearly shows that doxorubicin loaded on keratin nanoparticles (DOX-KNPs) has a lower $IC_{50}$ than that of free doxorubicin. This result indicates that the DOX-KNPs are more effective than free doxorubicin.

Evaluation of DOX accumulation was performed on MCF-7 and MDA-MB-231 cells seeded at the density of $3 \times 10^5$ cells/well in six-well plates and exposed to 1 µg/ml DOX and DOX-loaded KNPs for 2 h. Following this treatment, cells were rapidly washed with ice-cold PBS, detached with trypsin, re-suspended in ice-cold PBS, and analyzed by flow cytometry, using a Becton-Dickinson FACS Calibur equipped with a 15 mW, 488 nm, air-cooled argon ion laser. The fluorescence emission was collected through a 575 nm band-pass filter in log mode and DOX-fluorescence intensity was calculated from the flow cytometric profiles by the Cell Quest Pro software (Becton Dickinson). Control in FIG. 7B are untreated cells.

FIG. 7B shows that doxorubicin loaded on keratin nanoparticles obtained according to the present invention accumulate in the targeted cell similarly to free doxorubicin. In particular, DOXO internalization results higher in MDA-MB 231 cells when loaded onto the nanoparticles as respect to free DOX

Example 9—In Vitro Activity of Keratin Nanoparticles Loaded with Paclitaxel

The effect KNPs-PTX, on MCF-7 and MDA MB 231 cell growth in 2D model was evaluated by Acid phosphatase Assay Kit (APH, Sigma-Aldrich). Briefly $4.0 \times 10^3$ MCF-7 and $5.0 \times 10^3$ MDA MB 231 cells were seeded in 200 µl of growth medium in replicate (n=4) in a 48-well culture plate (TPP). After 48 h of cell growth, the medium was removed and the cells were incubated with the experimental medium containing KNPs-PTX at different PTX concentrations; e.g. 0.00002, 0.02 and 5 jg/ml. Seventy-two hours after treatment, APH assay was performed according manufacturer's instructions. Well absorbance was measured at 405 nm in a Synergy H1 Multi-Mode Reader (BioTek Instruments, Luzern, Switzerland).

Cell death was evaluated using the Annexin V-APC and Propidium Iodide (PI) Apoptosis Detection Kit (Becton Dickinson, BD, Allschwil, Switzerland). Briefly, $1.0 \times 10^5$ MCF-7 and MDA MB 231 in 2D model were treated with KER-NPs-PTX (PTX, 5 µg/mL). The cells were then washed twice with 1× annexin-binding buffer at 375 rcf for 5 min and were stained with APC-Annexin V and PI at 24 and 48 h. Samples were run on the flow cytometer at a 640 nm excitation to measure APC-Annexin V (FL4) and at 488 nm to measure PI (FL2), respectively. Any cell debris with low FSC and SSC was excluded from the analyses. Flow cytometry was carried out by a C6 flow cytometer (Accurri Cytometers, Milan, Italy) and the analysis was performed by a FCS Express 4 (BD Bioscience, Milan, Italy).

As shown in FIG. 8, KER-NPs-PTX are able to efficiently delivery PTX in MCF-7 and MDA MB 231 cells. In particular, in MCF-7 cells a similar effect was observed on cellular growth induced by the two formulations at the highest concentration, i.e 5 µg/ml, 72 h after treatment. Interestingly, in MDA MB 231 cells, KER-NPs-PTX at the highest considered concentration, i.e. 5 µg/ml, were able to induced a significant reduction in cell growth (p<0.001) as compared to PTX as free (p<0.001) (FIG. 8B).

Example 10—In Vitro Activity of Keratin Nanoparticles Loaded with (R)-9-Hydroxyl Stearic Acid, (R)-9-HSA on HT29 Cells Briefly $5.0 \times 10^3$ human colon adenocarcinoma cell line HT29 cells were seeded in 200 µl of growth medium in replicate (n=4) in a 48-well culture plate. After 24 h of cell growth, the medium was removed and the cells were incubated with the experimental medium containing KNPs-9HSA (50 µM of 9-HSA) and free 9-HSA. Twenty-four hours after treatment, cells were detached and counted.

9-hydroxystearic acid (9-HSA) belongs to a class of lipid peroxidation products identified in several human and murine cell lines. These products are greatly diminished in tumors compared to normal tissues and their amount is inversely correlated with the malignancy of the tumor. It is known that 9-HSA acts as a histone deacetylase 1 (HDAC1) inhibitor, thus resulting in an inhibition of proliferation together with an induction of differentiation of tumor cells.

FIG. 9 shows that KNPs-9HSA as well as free 9-HSA inhibit tumor cell proliferation, thus showing that there is no lowering of the 9-HSA activity when it is loaded on keratin nanoparticles according to the present invention.

Cell cycle analysis was performed as follows: $5.0 \times 10^3$ HT29 cells were seeded in 200 µl of growth medium in a 48-well culture plate. After 24 h of cell growth, the medium was removed and the cells were incubated with the experimental medium containing KER-NPs-9HSA (50 µM of 9-HSA) and free 9-HSA. Twenty-four hours after treatment, cells were trypsinized, washed twice with PBS and then centrifuged. Cells pellet was re-suspended in 0.01% Noni-det-P40 (Sigma-Aldrich), 10 µg/mL of RNasi (Sigma-Aldrich), 0.1% of sodium citrate (Sigma-Aldrich), 50 µg/mL di propidium iodide (PI) (Sigma-Aldrich), and kept in the dark for 30 min at room temperature. Florescence was detected by a flow cytometry (Beckman Coulter Epics XL-MCL), while cell cycle analysis was performed with Cell Cycle program (MODEFIT 5.0).

Figure 10:
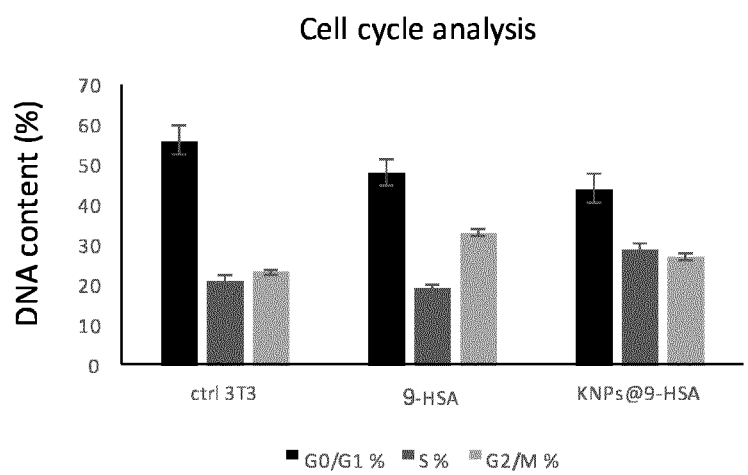
FIG. 10 shows bar graphs showing the cell cycle analysis on HT29 cells treated with 9-HSA as free or loaded on keratin nanoparticles.

FIG. 10 shows that, conversely to the effect exerted by free 9-HSA that blocks the cell cycle in the G0/G1 phase, once loaded on to keratin nanoparticles a higher number of cells arrest in the S phase, thus providing evidence of the stronger cytotoxic activity of the keratin-9HSA formulation.

RELEVANT DOCUMENTS

1. G. Gong, Y. Xu, Y. Zhou, Z. Meng, G. Ren, Y. Zhao, X. Zhang, J. Wu, and Y. Hu, *Molecular switch for the assembly of lipophilic drug incorporated plasma protein nanoparticles and in vivo image Biomacromolecules* 2012, 13(1), 23-28.
2. Q. Li, L. Zhu, R. Liu, D. Huang, X. Jin, N. Che, Z. Li, X. Qu, H. Kang, and Y. Huang, Biological stimuli responsive drug carriers based on keratin for triggerable drug delivery *J. Mater. Chem.* 2012, 22 (37), 19964.
3. H. Xu, Z. Shi, N. Reddy, and Y. Yang, Intrinsically water-stable keratin nanoparticles and their in vivo biodistribution for targeted delivery *J. Agric. Food Chem.* 2014, 62 (37), 9145-9150.
4. X. Zhi, Y. Wang, P. Li, J. Yuan, and J. Shen, Preparation of keratin/chlorhexidine complex nanoparticles for long-term and dual stimuli-responsive release *RSC Adv.* 2015, 5 (100), 82334-82341.
5. M. Curcio, B. Blanco-Fernandez, L. Diaz-Gomez, A. Concheiro, and C. Alvarez-Lorenzo, Hydrophobically Modified Keratin Vesicles for GSH-Responsive Intracellular Drug Release, *Bioconjug. Chem.*, 2015, 26(9), 1900-1907.
6. S. Kunjiappan, A. Chowdhury, B. Somasundaram, and C. Bhattacharjee, Optimization, preparation and characterization of rutin-quercetin dual drug loaded keratin nanoparticles for biological applications, *Nanomed. J.*, 2016, 3(4), 253-267.
7. E. Turner, L. Burnett, and S. K. Yazdani, Keratose as a Novel Drug Carrier for Drug Coated Balloons in 2016 32nd Southern Biomedical Engineering Conference (SBEC), 2016, pp. 71-72.
8. A. Vasconcelos, G. Freddi, A. Cavaco-Paulo Biodegradable Materials Based on Silk Fibroin and Keratin *Biomacromolecules,* 2008, 9, 1299-1305
9. Safety Assessment of Keratin and Keratin-Derived Ingredients as Used in Cosmetics http://www.cir-safety.org/supplementaldoc/safety-assessment-keratin-and-keratin-derived-ingredients-used-cosmetics-0
10. Aboushwareb, T.; Eberli, D.; Ward, C.; Broda, C.; Holcomb, J.; Atala, A.; Van Dyke, M. J. A keratin biomaterial gel hemostat derived from human hair: Evaluation in a rabbit model of lethal liver injury *J. Biomed. Mater. Res., Part B* 2009, 90, 45-54.
11. Yanmei Li, Xuelian Zhi, Jiantao Lin, Xin You, Jiang Yuan, Preparation and characterization of DOX loaded keratin nanoparticles for pH/GSH dual responsive release, Materials Science and Engineering: C, Volume 73, 1 Apr. 2017, Pages 189-197.
12. Clyne M. et al., Int. J. Mol. Sci. 2012, 13, 5554-5570; Ferrari, M. et al., *Nature Biotechnology*, 2015, 33(9), 941-951

The invention claimed is:

1. A nanoparticle comprising a keratin polypeptide and at least one lipophilic active ingredient, wherein
   said at least one lipophilic active ingredient is non-covalently bound to said keratin polypeptide,
   said keratin polypeptide is water-soluble, and
   said keratin polypeptide is a wild-type keratin polypeptide having a molecular weight higher than 14 kDa or a wild-type keratin polypeptide, having a molecular weight higher than 14 kDa which has been modified by chemical functionalization of the N-terminus with organic compounds and/or chemical functionalization of amino acid side chains therein with hydroxyl, amino and thiol groups.

2. The nanoparticle according to claim 1, wherein said at least one lipophilic active ingredient is selected from the group consisting of therapeutic agents, diagnostic agents, nutraceuticals, cosmetic ingredients, dyes and cosmeceuticals.

3. The nanoparticle according to claim 1, wherein said nanoparticle further comprises at least one hydrophilic active ingredient non-covalently bound to said keratin polypeptide.

4. The nanoparticle according to claim 3, wherein said at least one hydrophilic active ingredient is selected from the group consisting of therapeutic agents, diagnostic agents, nutraceuticals, cosmetic ingredients, dyes and cosmeceuticals.

5. The nanoparticle according to claim 2, wherein said at least one lipophilic active ingredient is a therapeutic agent selected from the group consisting of anticancer drugs, anti-inflammatory agents, antimicrobial agents, analgesics, hormones, anaesthetic agents, antianginals; anti-arrhythmic drugs; antibacterial and antiprotozoal agents; anti-coagulants; antidepressants; anti-diabetic drugs; anti-epileptic drugs; antifungal agents; antihistamines; anti-hypertensive drugs; anti-muscarinic agents; antineoplastic agents; anti-migraine drugs; anti-parasitic agents; anti-Parkinsonian drugs; antipsychotic, hypnotic and sedating agents; anti-stroke agents; anti-thrombotic agents; antitussives; antivirals; beta-adrenoceptor blocking agents; calcium channel blockers; cardiac inotropic agents; contraceptive agents; corticosteroids; dermatological agents; diuretics; gastro-intestinal agents; haemostatics; local anaesthetics; opioid analgesics; parasympathomimetics; peptides; steroids; stimulating agents; and vasodilators.

6. The nanoparticle according to claim 5, wherein said therapeutic agent is an anticancer drug, optionally selected from the group consisting of methotrexate, cisplatin; topotecan; 5-fluorouracil, thiotopotecan, thiocamptothecin, camptothecin, paclitaxel, docetaxel, doxorubicin, bicalutamide, MDV3100 enzalutamide, 9-hydroxyl stearic acid, curcumin, irinotecan hydrochloride, vinblastine, histone methyltransferases inhibitors, carboplatin, methylene blue, Azure A (N,N-dimethylthionine chloride), porphyrins and chlorins.

7. The nanoparticle according to claim 4, wherein said at least one hydrophilic active ingredient is a therapeutic agent selected from the group consisting of anticancer drugs, anti-inflammatory agents, antimicrobial agents, analgesics, hormones, anaesthetic agents, antianginals; anti-arrhythmic drugs; antibacterial and antiprotozoal agents; anti-coagulants; antidepressants; anti-diabetic drugs; anti-epileptic drugs; antifungal agents; antihistamines; anti-hypertensive drugs; anti-muscarinic agents; antineoplastic agents; anti-migraine drugs; anti-parasitic agents; anti-Parkinsonian drugs; antipsychotic, hypnotic and sedating agents; anti-stroke agents; anti-thrombotic agents; antitussives; antivirals; beta-adrenoceptor blocking agents; calcium channel blockers; cardiac inotropic agents; contraceptive agents; corticosteroids; dermatological agents; diuretics; gastro-intestinal agents; haemostatics; local anaesthetics; opioid analgesics; parasympathomimetics; peptides; steroids; stimulating agents; and vasodilators.

8. The nanoparticle according to claim 1, wherein said nanoparticle contains an amount of said at least one lipophilic active ingredient ranging from 5% to about 45% by weight of the weight of said nanoparticle.

9. The nanoparticle according to claim 1, wherein said nanoparticle has a diameter between 1 nm to 400 nm, or between 100-200 nm.

10. A pharmaceutical composition comprising the nanoparticles according to claim 5, and a pharmaceutically acceptable carrier.

11. A pharmaceutical formulation comprising the composition according to claim 10 for parenteral or oral administration.

12. A pharmaceutical composition comprising the nanoparticles according to claim 6, and a pharmaceutically acceptable carrier.

13. A pharmaceutical formulation comprising the composition according to claim 12 for parenteral or oral administration.

14. A cosmetic formulation for topical application, comprising the nanoparticles according to claim 4 and a cosmetically acceptable vehicle.

15. A cosmetic formulation for topical application, comprising the nanoparticles according to claim 2, and a cosmetically acceptable vehicle.

16. A functional food comprising the nanoparticles according to claim 1, wherein the functional food is selected from the group consisting of cereal bars, yogurt dairy products, bakery products, fruit juices and drinks.

17. A method for producing the nanoparticle according to claim 1, comprising:
   a) dissolving the keratin polypeptide in water or in a buffered aqueous solution at concentrations ranging from 1 to 5 mg/mL at room temperature, thereby obtaining a solution;
   b) filtering said solution; and
   c) adding said at least one lipophilic active ingredient previously dissolved in an organic solvent to said solution obtained in step b) under stirring.

18. A method of treating a patient suffering from a neoplastic disease, which comprises administering to the patient a therapeutically effective amount of the nanoparticle according to claim 6, wherein said neoplastic diseases are selected from the group consisting of breast cancer, ovarian cancer, prostate cancer, lung cancer, colon cancer, colorectal cancer, pancreatic cancer, gastrointestinal stromal tumor, adrenal cancer, skin melanoma, non-skin melanoma, mouth cancer, eye tumor, nasal cavity and paranasal sinus cancer, penile cancer, bronchial carcinoma, heart cancer, uterine body cancer, cervical cancer, esophageal cancer, liver cancer, metastatic pancreatic cancer, lymphomas, Hodgkin lymphoma, non-Hodgkin lymphoma, cutaneous lymphoma, pediatric lymphomas, laryngeal cancer, pharyngeal cancer, malignant mesothelioma, leukemias, hairy cell leukaemia, chronic lymphocytic leukaemia, Acute lymphoblastic leukaemia, acute myeloid leukaemia, chronic myeloid leukaemia, pediatric leukemia, multiple myeloma, sarcomas, gliomas, renal cancer, testicular cancer, thyroid cancer, soft tissue sarcoma, bone sarcoma, Ewing sarcoma, Kaposi sarcoma, extraskeletal Ewing sarcoma, chondrosarcoma, osteosarcoma, metastatic bone cancer, choriocarcinoma, pineal gland cancer, salivary gland tumors, hypophysis cancer, primitive neuroectodermal tumour, multiple endocrine neoplasia type 1 (MEN1), Multiple Endocrine Neoplasia Type 2 (MEN2), bladder cancer, tumors of the pelvic organs, ureteral cancer, oral cavity cancer, anal cancer, vulvar cancer, vaginal cancer, spleen cancer, brain tumors, embryonal tumors, gall-bladder cancer, bile duct cancer, cancer cachexia, neuroblastoma cancer, pediatric neuroblastoma cancer, neuroendocrine cancer, pediatric tumors and Myeloproliferative neoplasms.

19. A method comprising administering the nanoparticle according to claim 5 by topical application to a patient.

20. A method comprising administering to the patient a therapeutically effective amount of the pharmaceutical composition according to claim 10 to a patient by topical application.

\* \* \* \* \*